United States Patent
Grüning et al.

[11] Patent Number: 6,150,543
[45] Date of Patent: Nov. 21, 2000

[54] ENZYMATIC PREPARATION OF REGIOSELECTIVE FATTY ACID ESTERS OF ASCORBIC ACID

[75] Inventors: Burghard Grüning; Geoffrey Hills, both of Essen, Germany

[73] Assignee: Th. Goldschmidt Ag, Essen, Germany

[21] Appl. No.: 09/211,182

[22] Filed: Dec. 14, 1998

[30] Foreign Application Priority Data

Dec. 20, 1997 [DE] Germany .......................... 197 57 103

[51] Int. Cl.⁷ .......................... C07C 59/00; C07D 305/12
[52] U.S. Cl. ............................................ 554/148; 549/315
[58] Field of Search .................................. 554/219, 148; 549/315

[56] References Cited

FOREIGN PATENT DOCUMENTS

| 0 401 704 | 12/1990 | European Pat. Off. . |
| 27 43 526 | 4/1978 | Germany . |
| 33 08 922 | 9/1984 | Germany . |
| 4-141093 | 5/1992 | Japan . |
| WO 90/09451 | 8/1990 | WIPO . |

OTHER PUBLICATIONS

Humeau, C. et al., "Synthesis of 6–O–palmitoyl L–ascorbic acid catalyzed by Candida Antarctica Lipase", in *Biotechnology Letters*, vol. 17, No. 10 (Oct. 1995), pp. 1091–1094.

Haase, B. et al., "Enzymatische Synthesen von Zuckerestern", presented Jun. 30, 1997–Jul. 1, 1997 at 1st Workshop, "Bioconversion of Renewable Raw Materials".

*Primary Examiner*—Paul J. Killos
*Attorney, Agent, or Firm*—Scully, Scott, Murphy & Presser

[57] ABSTRACT

The invention relates to a process for the enzymatic preparation of regioselective fatty acid esters of ascorbic acid and selected fatty acid alkyl esters.

Ascorbic acid and fatty acid alkyl esters are reacted in a solvent or suspending agent at reduced pressure in relation to the atmosphere and temperatures above the boiling point of the resulting alcohol of reaction.

24 Claims, No Drawings

ENZYMATIC PREPARATION OF REGIOSELECTIVE FATTY ACID ESTERS OF ASCORBIC ACID

FIELD OF THE INVENTION

The invention relates to a process for the enzymatic preparation of regioselective fatty acid esters of ascorbic acid and selected fatty acid ascorbyl esters.

BACKGROUND OF THE INVENTION

The preparation of ascorbyl fatty acid esters chemically only takes place under extreme conditions, for example in sulfuric acid or in hydrogen fluoride, see, for example, DE 27 43 526 A1, DE 33 08 922 A1 or DE 28 54 353 C3. Processes of this type are questionable in their industrial implementation. The products need laborious purification. Products which are prepared by these processes have an odor which is not accepted by the user even after customary working up.

EP 0 401 704 B1 describes a process for the preparation of an organic ester of ascorbic acid comprising the reaction of ascorbic acid in the presence of 100 to 10,000 ppm of water and of an organic acid or an ester thereof in an organic solvent in the presence of an ester hydrolase. The yields reported here in Tables 1 to 4, however, do not exceed the value of 2%, so that this process has not found its way into industry.

C. Humeau et al., Biotechnology Letters, Vol. 17, No. 10, pp. 1091 to 1094 describe the synthesis of ascorbyl palmitate in a nonaqueous medium using an immobilized lipase, obtained from *Candida antarctica*, as a biocatalyst. The enzymatic synthesis is described as perfectly regioselective. It is stated that when using methyl palmitate as the acyl donor 68% of the ascorbic acid is converted. These values were obtained with an initial quantitative ratio of ascorbic acid to acyl donor of 1 mol to 5 mol and a very low use concentration. Reworking of the appropriate experiment, however, resulted in far lower reaction yields, so that this process is also not suitable for industrial preparation of the fatty acid esters of ascorbic acid.

In the papers of the meeting of the 1st workshop "Bioconversion of Renewable Raw Materials", Jun. 30th/Jul. 1st 1997 Detmold, pp. 57 and 58, enzymatic syntheses of sugar esters were presented by B. Haase et al. It is shown that it is increasingly possible by selective, enzyme (lipase)-catalysed esterifications to obtain better defined, even regioisomerically pure products. As an example of a sugar ester, a 6-O-acyl-L-ascorbic acid is mentioned without indication of an actual preparation process.

JP-A-4-141093; Mitsubishi Rayon Co. Ltd. describes the esterification of fatty acids with ascorbic acid using an enzymatic catalyst in a solvent which forms an azeotrope with water. The yield is only 37% after a reaction time of 72 h or 18% after the same reaction time if the water of reaction is not removed during the reaction. Moreover, the process necessitates the control of the water content in the reaction mixture in a concentration range from 200 to 2000 ppm.

BRIEF SUMMARY OF THE INVENTION

In contrast, the object of the present invention is to make available an improved process for the preparation of ascorbyl fatty acid esters in increased yields and in particular with respect to industrially relevant standards, and of novel substituted fatty acid ascorbyl esters.

The aforementioned object is achieved in a first embodiment of the invention by a process for the enzymatic preparation of regioselective fatty acid esters of ascorbic acid, fatty acid alkyl esters being transesterified with ascorbic acid in a solvent or suspending agent at reduced pressure in relation to that of the atmosphere at temperature above the boiling point of the resulting alcohol of reaction under the reaction conditions.

DETAILED DESCRIPTION OF THE INVENTION

The process according to the invention makes possible the preparation of novel and known ascorbyl fatty acid esters in increased yields relative to the prior art and in relatively large amounts. In a reaction mixture of ascorbic acid and a fatty acid alkyl ester, vacuum is applied to a reaction system having a suitable solvent or suspending agent in the presence of an enzyme which catalyses the esterification or transesterification reaction in order to distil off the liberated alcohol. This has the effect of displacing the reaction equilibrium to the product side, so that on the whole the yield of the product is markedly increased in relation to the prior art described in JP-A-4-141093. Using the present invention, yields in the range up to over 80% are surprisingly possible. It was found that the removal of the alcohol of reaction brings about an improvement in the process which markedly exceeds the improvement which can be derived in principle from the law of mass action. A possible cause could be the avoidance of the formation of strongly acidic water-containing ascorbic acid solutions. In contrast to that in JP-A-4-141093, the process according to the invention requires no monitoring of the water content, although as a result of the use of a reduced pressure water would optionally be removed together with other reaction products.

As stated above, it is known in the literature that lipases can catalyse the synthesis of 6-ascorbyl palmitate regiospecifically. The productivity of the reported reaction system, however, is not adequate for production on the industrial scale because of a) the low concentrations and b) the excessively low yields. In the process according to the invention, it is possible to employ higher concentrations and to achieve almost complete reactions of one of the reactants, namely of that found in excess.

In comparison with chemical processes, the enzymatic reaction is carried out under mild conditions and products of considerably better quality (odor-free) can therefore be prepared. The process according to the invention can be utilized particularly readily for the preparation of unsaturated fatty acid esters which are derived from oleic acid or linoleic acid.

Particularly preferred in the sense of the present invention and particularly highly suitable for use as antioxidants in foodstuffs and in cosmetics are regioselective fatty acid esters of ascorbic acid which are derived from fatty acid alkyl esters which are selected from straight-chain or branched, mono- or polyunsaturated, substituted or unsubstituted fatty acid radicals having 8 to 24 carbon atoms. Particularly preferred in the sense of the present invention are those ascorbic acid esters whose fatty acid radicals have 12 to 18 C atoms. The alkyl radicals of the fatty acid alkyl esters preferably have 1 to 3 C atoms in the alkyl radical. Particularly preferred in this sense are esters of methanol. Using the present invention, unsaturated, substituted fatty acid ascorbyl esters, for example hydroxy-substituted esters, such as ricinoleic esters, can be prepared particularly readily.

As ascorbic acid, preferably L-ascorbic acid or D-ascorbic acid is employed, in particular L-ascorbic acid.

The quantitative ratio of ascorbic acid to fatty acid alkyl ester can vary within a wide range. Thus a particularly preferred embodiment of the present invention consists in setting the quantitative ratio of ascorbic acid to fatty acid alkyl ester in the range from 10 mol:1 mol to 1 mol:10 mol. Particularly preferably, in this sense the quantitative ratio is set in the range from 1 mol:1 mol to 1 mol:5 mol.

The enzymes to be employed according to the present invention are known in the prior art and commercially available. For example, on p. 8 in the second paragraph WO 90/09451 describes appropriate enzymes which are also obtainable under the name Novozym®435 or Chirazyme L-2. In the mentioned WO 90/09451 enzymes, in particular immobilized enzymes, are described which are selected from lipases, esterases or proteases. Particularly preferred in the sense of the present invention are lipases having defined enzyme catalysis reactivity for ester bonds, in particular hydrolysis, synthesis and/or exchange of ester bonds. The product Novozym®435 of Novo Nordisk is an immobilized thermostable lipase system which is commercially available and is particularly preferably employed in the sense of the present invention.

The nature of the solvent or suspending agent can be varied within wide ranges in the sense of the present invention. If appropriate, a liquid reactant, such as a fatty acid alkyl ester, can also serve as a solvent or suspending agent, in particular for ascorbic acid, if the desired product dissolves adequately in the system. Particularly preferably in the sense of the present invention, solvents or suspending agents are employed whose boiling points are above, in particular at least 10° K. above, the boiling point of the resulting alcohol of reaction under the reaction conditions. If in the sense of the present invention the distillative removal of the alcohol of reaction is demanded, under this is to be understood all customary processes which are familiar to the average person skilled in the art having basic chemical knowledge. For example, the azeotropic removal of the alcohol of reaction using suitable entraining agents, pervaporation or the use of adsorbents is included here. Particularly preferably in the sense of the present invention, the solvent or suspending agent is selected from alcohols, ketones or ethers, particularly preferably from tertiary alcohols, since these have a particularly high boiling point. 2-Methyl-2-butanol, dipropyl ether, 2-butanone and ethylene glycol dimethyl ether are particularly to be mentioned here.

The solvent or suspending agent can also contain emulsifiers or surfactants which serve as additional dispersing agents for the ascorbic acid. In the sense of the invention, surfactant compounds, such as, for example, nonionic surfactants, fatty acid or fatty alcohol ethoxylates, alkyl polyglucosides or polyglycerol esters, anionic surfactants such as fatty acid salts, alkyl sulfates, alkyl phosphates and also the fatty acid ascorbyl esters themselves, and zwitterionic surfactants, such as cocoamidopropylbetaine or amine oxides may be mentioned.

Following the reaction, which is preferably carried out at a temperature in the range from 20 to 90° C., in particular in a temperature range from 40 to 70° C., the ester obtained can be worked up by processes known per se. The esterification reaction itself is preferably carried out at a pressure of less than 1 bar, in particular of less than 400 mbar, preferably less than 250 mbar. As is known, the lower the pressure, the lower the temperature necessary in order to remove the alcohol of reaction from the mixture by distillation.

Using the present invention, it is possible to react highly concentrated suspensions of ascorbic acid in the selected solvent or suspending agent. Particularly preferably in the sense of the present invention, ascorbic acid is therefore employed in an amount from 1.5 to 70% by weight, in particular 1.5 to 50% by weight, based on the amount of the solvent or suspending agent.

WORKING EXAMPLES

Example 1

6-ascorbyl palmitate 5.76 g of ascorbic acid was stirred in 44.23 g of methyl palmitate and 144 ml of 2-methyl-2-butanol at 70° C. 1 g of the catalyst Novozym®435 was then added and a vacuum of 200 mbar was applied. During the reaction period of 15 hours, the resulting methanol was distilled off through a Vigreux column. After completion of the reaction, the catalyst was filtered off and the 2-methyl-2-butanol was distilled off. Hexane was added to the residue, as a result of which the insoluble product 6-ascorbyl palmitate was precipitated. 10.8 g of the product were obtained, corresponding to a yield of 80%, based on ascorbic acid.

Example 2

6-ascorbyl ricinoleate 5.5 g of ascorbic acid was stirred at 70° C. in 39 g of methyl ricinoleate and 155.5 ml of 2-methyl-2-butanol. 1 g of the catalyst Novozym®435 was then added and a vacuum of 250 mbar was applied. During the reaction period of 20 hours, the resulting methanol was distilled off through a Vigreux column. The catalyst was then filtered off and the 2-methyl-2-butanol was distilled off. The product was purified using hexane. 11.8 g of the product was obtained, corresponding to a yield of 83%, based on ascorbic acid.

What is claimed is:

1. A process for the enzymatic preparation of regioselective fatty acid esters of ascorbic acid, comprising reacting ascorbic acid and at least one fatty acid alkyl ester in the presence of a catalytically effective amount of an enzyme in a solvent or suspending agent at reduced pressure in relation to that of the atmosphere and at temperatures above the boiling point of the resulting alcohol of the reaction, wherein said reduced Pressure is less than 1 bar.

2. The process as claimed in claim 1, wherein ascorbic acid is reacted with one or more fatty acid alkyl esters which are selected from esters having straight-chain or branched, mono- or polyunsaturated, substituted or unsubstituted fatty acid radicals having 8 to 24 C atoms.

3. The process as claimed in claim 1, wherein one or more fatty acid alkyl esters are employed whose fatty acid radicals have 12 to 18 C atoms.

4. The process as claimed in claim 1, wherein one or more fatty acid alkyl esters are employed whose alkyl radicals have 1 to 3 C atoms.

5. The process as claimed in claim 1, wherein one or more unsaturated, substituted fatty acid alkyl esters are employed.

6. The process as claimed in claim 1, wherein one or more unsaturated, hydroxy-substituted fatty acid alkyl esters are employed.

7. The process as claimed in a claim 6, wherein a ricinoleic acid ester of ascorbic acid is prepared.

8. The process as claimed in claim 1, wherein the quantitative ratio of ascorbic acid to fatty acid alkyl ester is in the range from 10 mol:1 mol to 1 mol:10 mol.

9. The process as claimed in any of claims 2–7, wherein the quantitative ratio of ascorbic acid to fatty acid alkyl ester is in the range from 10 mol:1 mol to 1 mol:10 mol.

10. The process as claimed in claim 8, wherein the quantitative ratio is in the range from 1 mol:1 mol to 1 mol:5 mol.

11. The process as claimed in any of claims 1 to 8, wherein hydrolases are employed which are selected from lipases, esterases or proteases.

12. The process as claimed in one of claims 1 to 8, wherein immobilized hydrolases are employed which are selected from lipases esterases or proteases.

13. The process as claimed in claim 1, wherein a solvent or suspending agent is employed whose boiling point is above the boiling point of the resulting alcohol of reaction.

14. The process as claimed in claim 13, wherein a solvent or suspending agent is employed whose boiling point is at least 10° K. above the boiling point of the resulting alcohol of reaction.

15. The process as claimed in claim 1, wherein said solvent or suspending agent is selected from ketones and ethers, and tertiary alcohols.

16. The process as claimed in claim 1, wherein said solvent or suspending agent is selected from 2-methyl-2-butanol, dipropyl ether, 2-butanone and ethylene glycol dimethyl ether.

17. The process as claimed in claim 1, wherein the reaction is carried out at a temperature in the range from 20 to 90° C.

18. The process as claimed in claim 1, wherein the reaction is carried out at a temperature in the range from 40 to 70° C.

19. The process as claimed in claim 1, wherein the reaction is carried out at a pressure of less than 400 mbar.

20. The process as claimed in claim 1, wherein the reaction is carried out at a pressure of less than n 250 mbar.

21. The process as claimed in claim 1, wherein ascorbic acid is employed in an amount from 1.5 to 70% by weight based on the amount of the solvent or suspending agent.

22. The process as claimed in claim 1, wherein ascorbic acid is employed in an amount from 1.5 to 50% by weight based on the amount of the solvent or suspending agent.

23. A regioselective fatty acid ester of ascorbic acid having at least one straight-chain or branched, mono- or polyunsaturated, substituted fatty acid radical having 8 to 24 C atoms, wherein at least one of the fatty acid radicals are hydroxy-substituted.

24. An ascorbyl ricinoleate comprising at least one straight-chain or branched, mono- or polyunsaturated, substituted fatty acid radical having 8 to 24 C atoms, wherein at least one of the fatty acid radicals are hydroxy-substituted.

* * * * *